United States Patent
Chandrasekaran et al.

(10) Patent No.: US 8,626,258 B2
(45) Date of Patent: Jan. 7, 2014

(54) SELF-ADHERING ELECTRODES AND METHODS OF MAKING THE SAME

(75) Inventors: Shankar Chandrasekaran, Bangalore (IN); Nikhil Subhashchandra Tambe, Bangalore (IN); Donald Eugene Brodnick, Cedarburg, WI (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 13/532,099

(22) Filed: Jun. 25, 2012

(65) Prior Publication Data

US 2012/0265046 A1   Oct. 18, 2012

Related U.S. Application Data

(62) Division of application No. 11/608,293, filed on Dec. 8, 2006, now Pat. No. 8,238,995.

(51) Int. Cl.
*A61B 5/0408* (2006.01)
*A61B 5/0478* (2006.01)

(52) U.S. Cl.
USPC ........... 600/373; 600/386; 600/393; 600/396; 977/925

(58) Field of Classification Search
USPC ................. 600/373, 393, 386, 396; 977/925
See application file for complete search history.

(56) References Cited

U.S. PATENT DOCUMENTS

| | | | |
|---|---|---|---|
| 6,334,856 B1 * | 1/2002 | Allen et al. | 604/191 |
| 6,622,035 B1 | 9/2003 | Merilainen et al. | |
| 6,690,959 B2 * | 2/2004 | Thompson | 600/372 |
| 6,743,211 B1 | 6/2004 | Prausnitz et al. | |
| 6,961,603 B2 * | 11/2005 | Merilainen | 600/383 |
| 7,266,410 B2 * | 9/2007 | Chen | 607/3 |
| 7,941,201 B2 * | 5/2011 | Chiou et al. | 600/373 |
| 2003/0050550 A1 | 3/2003 | Schmidt et al. | |
| 2004/0054393 A1 | 3/2004 | Stemme et al. | |

FOREIGN PATENT DOCUMENTS

| | | |
|---|---|---|
| JP | 1277536 A | 11/1989 |
| JP | 7284481 A | 10/1995 |
| JP | 2001057967 A | 3/2001 |
| JP | 2003124767 A | 4/2003 |
| JP | 2003520094 A | 7/2003 |

OTHER PUBLICATIONS

Notice of Allowance from corresponding JP Application No. 2007-313010 dated Sep. 11, 2012.
S. Chandrasekaran, et al., "Surface Micromachined Metallic Microneedles", J. of Microelectromechanical Systems, vol. 12, No. 3, Jun. 2003, pp. 281-288.
G. Ruffini, et al., "Enobio-Dry Electrophysiology Electrodes Using Carbon Nanotubes", Starlab, University of Barcelona, Sep. 13, 2005, pp. 1-24.

* cited by examiner

*Primary Examiner* — Lee S Cohen
(74) *Attorney, Agent, or Firm* — Jenifer Haeckl

(57) ABSTRACT

A self-adhering sensor for non-invasively attaching to a portion of a skin is provided. The sensor comprises a biocompatible substrate, and an array of solid nanoelectrodes coupled to the biocompatible substrate and configured to self-adhere to the skin. Also provided is a sensor for attaching to a portion of a skin, where the sensor comprises an array of solid electrodes configured to self-adhere to the skin, where each of the solid structures comprises a stem and one or more projections extending out from the stem, where both the stem and the projections are solid. The stem comprises a mechanical stopper to control the extent of penetration of the solid electrodes into the skin. The sensor further comprises an electrolyte coating disposed on one or more of the solid structures.

9 Claims, 15 Drawing Sheets

SELF-ADHERING ELECTRODES AND METHODS OF MAKING THE SAME

This application is a Division of patent application Ser. No. 11/608,293, filed Dec. 8, 2006, now U.S. Pat. No. 8,238,995.

BACKGROUND

The invention relates generally to healthcare applications, and more particularly to sensors in medical monitoring.

Various medical procedures require continued monitoring of patients. For example, when the patients are unable to take care of themselves, the patients may be monitored using a variety of monitoring devices (e.g., by remote monitoring) to ensure their well-being. This kind of monitoring may be for the bed-ridden patients or for the mobile patients as well. Such devices may monitor, ventilation, oxygenation, metabolism, blood circulation, electrocardiography (ECG), and electroencephalography (EEG). ECG devices monitor the activity of the heart, whereas EEG devices monitor the activity of the brain. Both ECG and EEG employ sensors that can pickup electrical signals from the corresponding organs in the body. These electrical signals are generally low level. For example, the electrical signal from the heart is about 0.5 milli volts to 2 milli volts, and the signal from the brain is a few hundred microvolts. Accordingly, it is desirable to have optimum skin preparation and electrode placement to avoid weakening and artifacts of these signals at the skin-electrode interface. A good contact between the sensor and the skin is desirable for good signal acquisition. Failure to have a good or continuous contact between the sensor and the skin can cause signal loss. Also, failure to securely attach the sensor to the skin can introduce artifacts into the signals. These artifacts may cause the system to generate false calls or suspend analysis.

In conventional sensors, adhesive materials are used to couple the electrodes to the skin. Depending on the application, the adhesives may vary in shape and tack strength. As used herein, the term "tack strength" refers to "stickiness" of adhesive material, and is a measurement of the strength of adhesion. For short-term ECG recordings (few seconds), the electrodes may be smaller and need not employ high strength adhesive because the patient will generally be still during this short period. However, the adhesive material, such as an adhesive gel, employed to couple the electrode to the skin, may dry out during the recording. Therefore a technician is required to continuously monitor and, if required, repair any electrode dislocations. For long term recordings, the electrode is more likely to suffer from disturbances caused by tugging, jostling, inadvertent scratching, clothing changes. During these disturbances the electrode may be inadvertently detached from the skin and coupling the electrode again to the skin using the same adhesive material may not have desirable results. Moreover, sudden detachment of the electrode may injure the patient. Adhesive materials may also cause rashes or other skin irritations. Adhesives may also cause injury and pain when the sensor is removed from the skin. For example, in neo-natal applications, removing sensors from the soft skin of a newborn without injuring the skin is difficult at best.

Accordingly, it is desirable to have a sensor that may be easily coupled and detached from the skin and which is configured to attach to the skin for extended period of time.

BRIEF DESCRIPTION

In an exemplary embodiment, a self-adhering sensor for non-invasively attaching to a portion of a skin is provided. The sensor comprises a biocompatible substrate, and an array of solid nanoelectrodes coupled to the biocompatible substrate and configured to self-adhere to the skin.

In another exemplary embodiment, a sensor for attaching to a portion of a skin is provided. The sensor includes an array of solid electrodes configured to self-adhere to the skin, where each of the solid structures comprises a stem and one or more projections extending out from the stem, where both the stem and the projections are solid. The stem comprises a mechanical stopper to control the extent of penetration of the solid electrodes into the skin. The sensor further comprises an electrolyte coating disposed on one or more of the solid structures.

In another exemplary embodiment, a method of non-invasively coupling a sensor to a portion of the skin is provided. The method comprises providing a sensor comprising a biocompatible substrate, and an array of solid nanoelectrodes configured to self-adhere to the skin, wherein the solid nanoelectrodes are coupled to the substrate. The method further comprises coupling the sensor by pressing the sensor against the surface of the skin so that at least a portion of one or more of the nanoelectrodes engages the surface of the skin.

In another exemplary embodiment, a method of coupling a sensor array to a portion of the skin is provided. The method comprises providing a sensor array. The sensor array comprises an array of solid structures configured to self-adhere to the skin, wherein each of the solid structures comprises a stem and one or more projections extending out from the stem, wherein both the stem and the projections are solid, and wherein the stem comprises a mechanical stop to control the amount of penetration of the solid structures into the skin. The sensor array further comprises an electrolyte coating disposed on one or more of the solid structures. The method further comprises pressing the sensor array against the surface of the skin so that the distal ends of the solid structures engage the surface of the skin while the mechanical stop is seated on the outside surface the skin.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Monitoring a patient may be desired under various circumstances. Monitoring for different functions of the body is accomplished using various pathways. Some of the monitoring may be non-invasive, for example, blood circulation may be monitored by monitoring blood pressure externally. Yet, skin sensors are employed to evaluate/read organ function. For example, skin sensors may be employed for monitoring the function of the heart and brain.

Electrocardiography (ECG) is a technique used to monitor heart activity. The heart is a muscle that has an electrical field having a current flow. The electrical activity of the heart may be detected by placing electrodes on the skin. The ECG signals can be measure between one or more pairs of electrodes placed on the human body. Each pair contains two electrodes of opposite polarity that are in electrical communication. By positioning the electrode at different locations, the clinician may monitor different views of the heart's electrical activity. Typically, the measurements are taken in a negative electrode to positive electrode direction. The positive and negative electrodes are disposed at different positions on the body. Also, more than one pair of electrodes may be applied to pick up the ECG signal. In an exemplary embodiment, a pair of electrodes is employed by disposing a negative electrode on the right arm and a positive electrode on the left arm.

Figure 1:
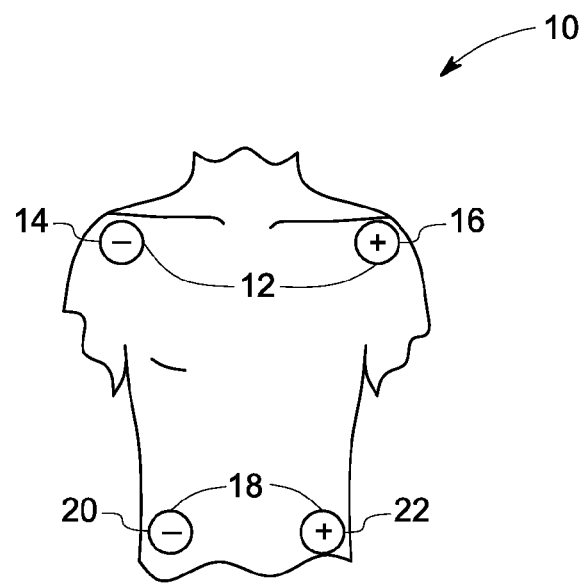
FIG. 1 is a schematic illustration of a portion of a human body employing an embodiment of the sensors of the invention.

FIG. 1 illustrates a portion of a human body 10 employing two pairs 12 and 18 of electrodes. The pair 12 includes a negative electrode 14 employed on the right shoulder and a positive electrode 16 employed on the left shoulder. The second pair 18 includes a negative electrode 20 employed on the right side of the torso and a positive electrode 22 employed on the left side of the torso. Depending on the position of these electrodes on the body, the ECG signals may have different shapes and amplitudes. Additionally, a third electrode also referred to as a reference electrode may also be employed. The reference electrode may be maintained at neutral and is used to reduce electrical interference. The ECG measures and records the electrical impulses when they are conducted through different parts of the heart. As noted above, the electrical signals generated by the heart are weak and therefore require good contact between the skin and the sensor employing the electrode.

Figure 2:
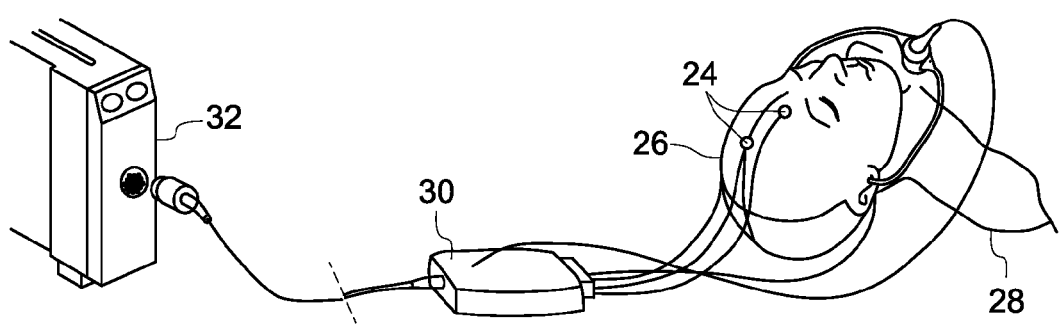
FIG. 2 is a schematic illustration of an embodiment of the sensor system of the invention.

Brain activity may be monitored using electroencephalography (EEG). Neurons transmit electrical pulses when they communicate with each other. EEG measures the spontaneous electrical activity of the cerebral cortex, i.e., the surface layer of the brain. Similar to ECG, EEG is also measured as a voltage differential between two electrodes. To attach the electrodes that employ adhesive materials, the dead cells and grease are first removed from the skin surface to facilitate adhesion. Conductive gel or paste may also be used to improve the contact between the skin and the electrodes. FIG. 2 illustrates a set up for taking ECG measurements. Sensors 24 are fixed to the forehead 26 of a human being 28. The signals captured by the sensors 24 are very low; hence an amplifier 30 is employed to boost the signals. The signals are then processed using the processor 32 and displayed.

In some of the embodiments, the sensors do not employ adhesive materials. The sensors are self-adhering. As used herein, the term "self-adhering" embodies structures which are configured to couple to a surface and do not need additional means for coupling the structures to the surface. For example, the self-adhering electrodes may be coupled to the surface without employing any adhesive materials.

Although, the exemplary embodiments described and illustrated are described in the context of ECG and EEG applications, these examples are not limiting. The self-adhering sensors may be used in a variety of other medical and non-medical applications. For example, the self-adhering devices and methods may be used to measure, the saturation of oxy-hemoglobin (SpO2) or even to fix or adorn the skin or other similar surfaces with any number or type of items with which adhesives are not a desirable means of fixing.

In one or more of the embodiments, the self-adhering sensor for non-invasively attaching to a portion of a skin includes a biocompatible substrate having an array of solid nanoelectrodes. As used herein, the term "solid nanoelectrodes" refer to nanoelectrodes that have a solid core and are not hollow from inside. The biocompatible substrate may comprise any material that has the ability to be brought in contact with the skin without causing the body to attack, reject, or react against the substrate. In certain embodiments, the substrate may comprise, but is not limited to, a ceramic, metal, or a polymeric material, or combinations thereof. For example, the substrate may comprise a plastic. As will be described in detail below, the solid nanoelectrodes are configured to self-adhere to the skin.

Figure 3:
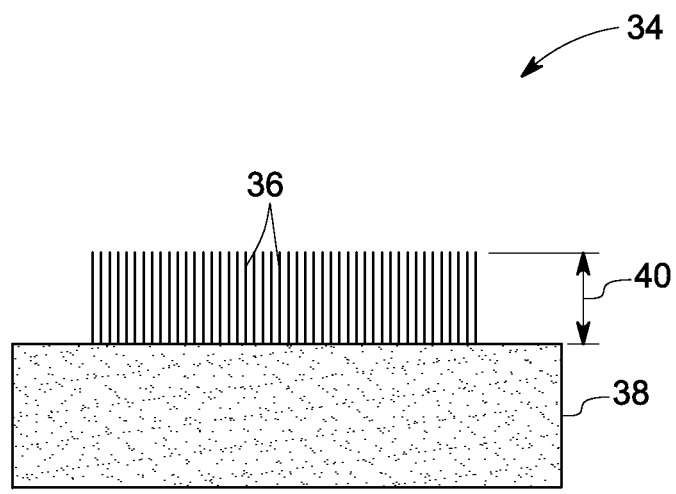
FIG. 3 is a cross-sectional view of a self-adhering non-invasively coupled sensor, in accordance with embodiments of the invention.

FIG. 3 illustrates a side view of a self-adhering sensor 34. The sensor 34 may be non-invasively coupled to a portion of the skin. In the presently contemplated embodiment, the sensor 34 includes a plurality of nanoelectrodes 36. In some of the embodiments, the nanoelectrodes 36 comprise solid nanostructures. The nanoelectrodes 36 preferably comprise biocompatible materials. In some embodiments, the nanoelectrodes 36 are made of electrically conductive material, such as metals. For example, the nanoelectrodes 36 may be made of, but not limited to, silver, gold, platinum, alloys of palladium and cobalt, stainless steel, noble metals, conductive polymers, or combinations thereof. In other embodiments, the nanoelectrodes 36 may comprise conductive materials, which may or may not be biocompatible depending on the material and the application. If not biocompatible, the nanoelectrodes 36 may comprise a coating of a biocompatible material to avoid any reactions that may otherwise occur if the non-biocompatible material is brought in contact with the skin.

In some of the embodiments, the cross-section of the solid nanoelectrodes 36 may comprise the same or differing geometric shapes. For example, in one embodiment, the sensor may comprise a combination of different geometrical shapes, such as, but not limited to, circular, triangular, hexagonal, square, or rectangular shapes.

In some of the embodiments, the nanoelectrodes 36 may have a length, shown by arrow 40, of less than or equal to about 5 micrometers. In one example, the length of the nanoelectrodes 36 is less than or equal to about 1 micrometer. The length of the nanoelectrodes may be chosen so as to avoid collapsing/buckling of the nanoelectrodes. The diameter of these nanoelectrodes is preferably in a range from about 10 nanometers to about 500 nanometers. The combination of length and diameter may be chosen so as to provide an aspect ratio in a range from about 1:2 to about 1:20. In one example, the aspect ratio may be in a range from about 1:5 to about 1:10. Lower aspect ratios may be desirable while employing conductive polymers due to the lower strength of the polymers.

In some of the embodiments, the array of nanoelectrodes 36 in the sensor 34 may comprise nanoelectrodes 36 having varied diameters. Alternatively, all the nanoelectrodes 36 in the array of the sensor 34 may have same diameters. Further, the spacing between any two nearest nanoelectrodes 36 is preferably about a few hundred nanometers. As used herein, the spacing is the distance from the outer surface of one nanoelectrode to the outer surface of another nanoelectrode. For example, nanoelectrodes 36, having a diameter of about 200 nanometers, are preferably positioned at a distance of about 100 nanometers from the nearest neighbors. The spacing and the diameters may be chosen to provide sufficient surface-to-surface contact when the sensor 34 is brought into contact with the skin. The area of the sensor 34 may be in a range from about $1 \times 1$ cm$^2$ to about $3 \times 3$ cm$^2$.

The sensor 34 is disposed on the skin such that the nanoelectrodes 36 are closer to the skin than to the substrate 38. In one example, the substrate 38 comprises a polymer, a ceramic, or a printed circuit board. Van der Waals forces are optimized between the nanoelectrodes 36 and the skin when the sensor 34 is disposed close to the skin or brought in contact with the skin. Van der Waals forces in part enable coupling of the sensor 34 to the skin without the need to use adhesive materials. Nanoelectrodes 36 also do not require invasive techniques, and therefore, the sensor 34 can be easily coupled to and detached from the skin. Accordingly, the sensor 34 may be used in neo-natal healthcare applications. In such applications, the sensors 34 may be easily removed from the soft skin of the baby as compared to the other sensors that employ adhesive materials as a coupling means for adhering to the skin. Unlike adhesives that lose their tack strength in a short period of time, sensor 34 may be used for an extended period of time. Some or all of the nanoelectrodes 36 in the sensor 34 may also provide other functionality in addition to adhesion and electrical conductivity functions, such as, but not limited to, thermal conductivity.

Figure 4:
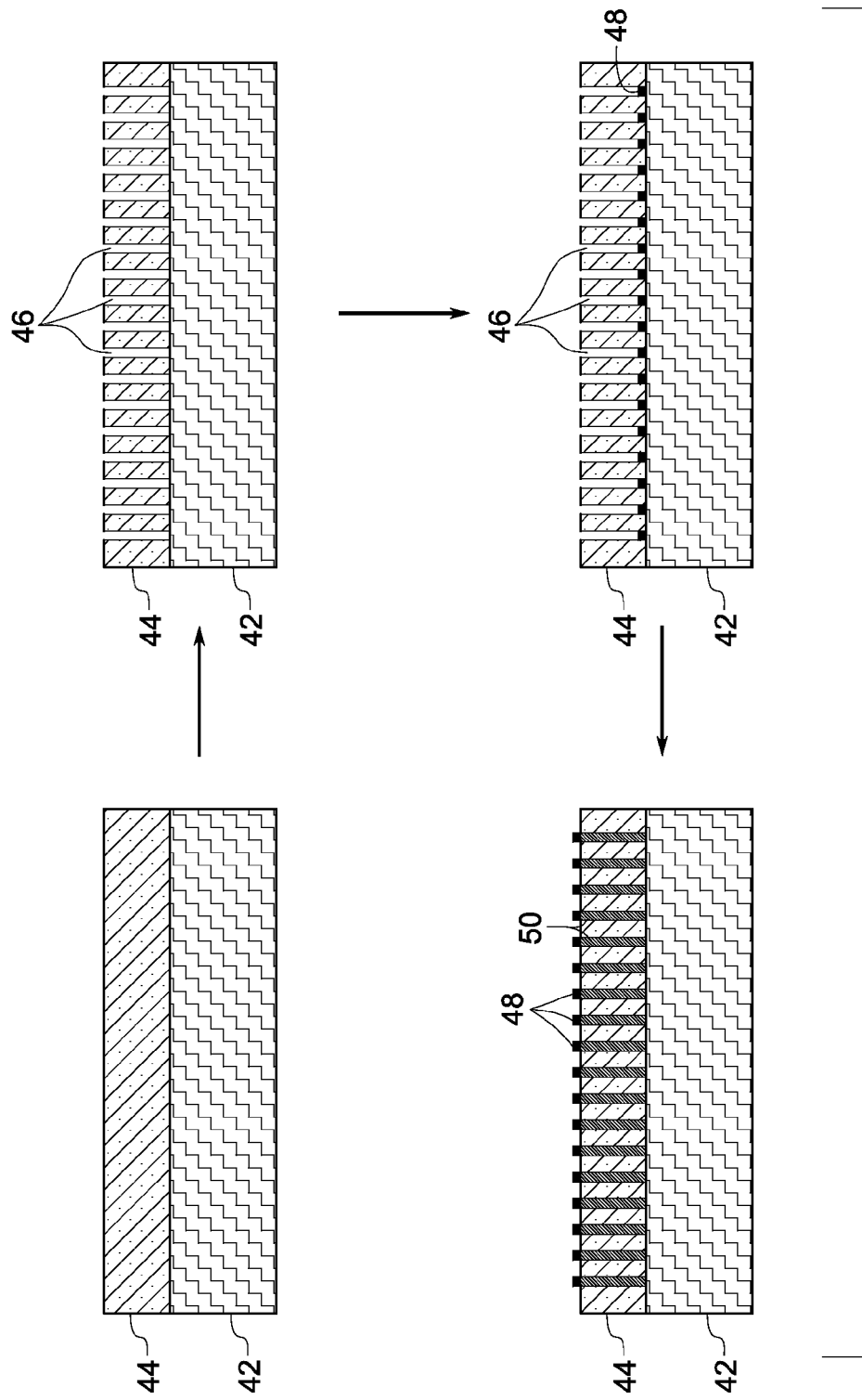
FIGS. 4-6 are schematic illustrations of various steps involved in an exemplary method of the invention for making the sensor of FIG. 3, in accordance with one or more embodiments.
Figure 5:
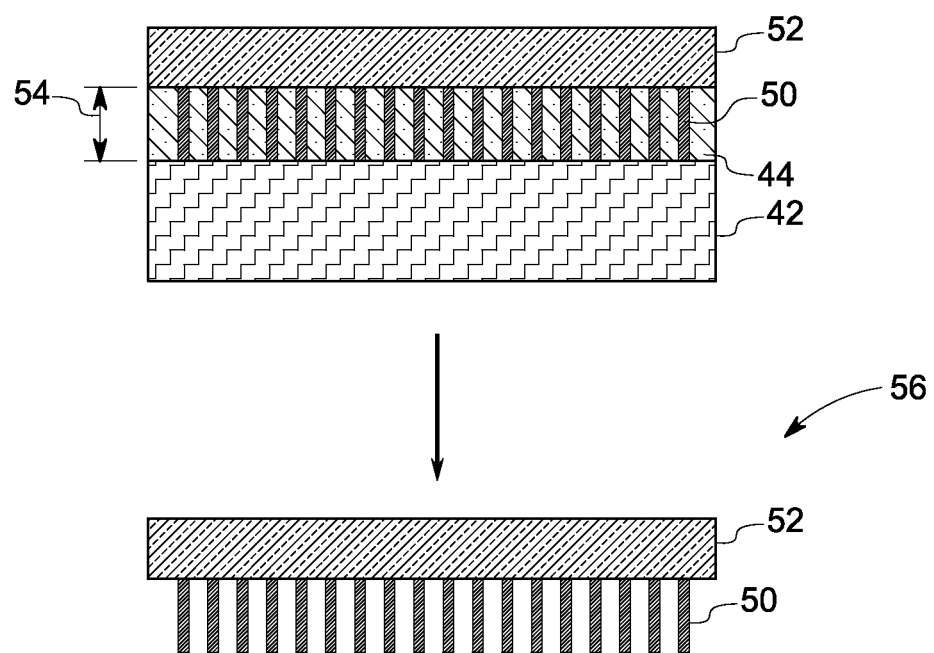
Figure 6:
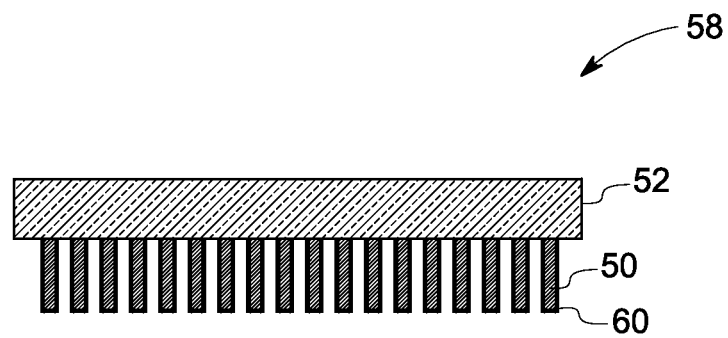

In some of the embodiments, sensors comprising solid nanoelectrodes, such as nanoelectrodes 36, may be formed using the method illustrated in FIGS. 4-6. FIGS. 4-6 illustrate various steps involved in the method of making the nanoelectrodes 36. FIG. 4 illustrates the steps of growing nanostructures that can be used as nanoelectrodes. In the illustrated embodiment, a substrate 42 is provided. In one example, the substrate may be a semiconductor substrate. For example, the substrate may include materials, such as but not limited to, silicon, gallium arsenide, aluminum gallium arsenide, or combinations thereof. Next, a metal film 44, comprising aluminum, is deposited on the substrate 42. In some embodiments, the metal film 44 is configured to develop pores 46 upon anodization or oxidation. In one embodiment, anodization of the metal film 44 may be performed by employing processes, such as wet chemical processes. In an exemplary embodiment, the metal may include aluminum, which upon oxidation may convert into porous alumina with uniform vertical channels. In some embodiments, the pore density of the anodized alumina may be in a range from about $10^7$ pores/cm$^2$ to about $10^{11}$ pores/cm$^2$. Alternatively, a porous template layer, such as anodic aluminum oxide layer, may be attached directly onto the substrate 42. Although not illustrated, an additional dissolvable metal layer may be deposited between the metal film 44 and the substrate 42. In some embodiments, this dissolvable metal layer may be dissolved in certain solutions, thereby detaching the metal film 44 from the substrate 42, as described below. In some embodiments, the metal layer may include metals, such as but not limited to, titanium, chromium, tungsten, titanium-tungsten, copper, gold, or combinations thereof.

Further, a catalyst 48, such as gold may be deposited in the pores 46. In some embodiments, the catalyst 48 may be deposited by employing processes, such as electrochemical deposition, e-beam evaporation, thermal evaporation, or sputtering. The catalyst 48 may be used to facilitate the growth of the nanoelectrodes. The fill factor of the catalyst 48 and/or the nanostructures 50 may be reduced to increase the space between individual nanowires. For example, the fill factor of the catalyst 48 may be reduced by using an easily oxidizing metal layer, such as titanium. Further, if a catalyst 48, such as gold, is employed, the catalyst 48 is heated to form a liquid droplet and absorb the material of the nanoelectrodes and deposit it on the substrate 42.

Next, nanostructures 50 are deposited in the pores 46 having the catalyst 48. In some embodiments, the nanostructures 50 may be made of a biocompatible material. For example, silicone elastomer, ethylene-vinyl acetate copolymer, hexamethyldisiloxane, or silazane. In other embodiments, the nanostructures 50 may be made of a material that is not biocompatible. For example, in these embodiments, the nanostructures 50 may include silicon, germanium, group III-V semiconductors, group II-VI semiconductors, group IV-IV semiconductors, or combinations thereof. As will be described with regard to FIG. 6, in the embodiments where a non-biocompatible material is employed in the nanostructures 50, a thin film 60 of a biocompatible material may be deposited on the nanostructures 50. In some embodiments, the nanostructures 50 may be deposited using chemical vapor deposition, such as one using vapor-liquid-solid mechanism. In these embodiments, the substrate 42 having the catalyst 48 in the pores 46 may be transferred to a chemical vapor deposition chamber prior to depositing the nanostructures 50.

In some embodiments, the nanostructures 50 may not have a uniform length, thereby making it difficult to ensure a good contact between the sensor and the skin. As used herein, the term "uniform length" embodies a difference of up to about 50 nanometers in the length of the nanoelectrodes. Although not illustrated, prior to depositing the sensor substrate 52 (FIG. 5), the lengths 54 of the nanostructures 50 may be made uniform by etching away a portion of the structures 50. The length 54 of the nanostructures 50 may be made uniform by depositing a photoresist or other polymer filling material around the nanostructures 50 up to a desired length. For example, the photoresist layer may be spin coated on the nanostructures 50. The photoresist layer may be deposited at low temperatures in a range from about 46° C. to about 100° C. In some of the embodiments, oxygen plasma may be employed to etch the extended portions of the nanostructures 50 having uniform length. In other embodiments, wet etch may be employed to etch away the extended portions of the nanostructures 50, thereby forming the nanostructures 50 having uniform lengths. Subsequently, the photoresist is removed by dissolving it in a suitable solvent, such as acetone, or other resist strippers, or etching by oxygen plasma.

FIG. 5 illustrates steps of depositing a sensor substrate 52 that is configured to hold the nanostructures 50 together to form a sensor, such as the sensor 34 (see FIG. 3). The sensor substrate 52 includes ceramic, silicon, or a printed circuit board. The sensor substrate 52 may be deposited by any of the deposition techniques such as physical vapor deposition, plasma-enhanced chemical-vapor deposition (PECVD), radio-frequency plasma-enhanced chemical-vapor deposition (RFPECVD), expanding thermal-plasma chemical-vapor deposition (ETPCVD), reactive sputtering, electron-cyclodrawn-residence plasma-enhanced chemical-vapor deposition (ECRPECVD), inductively coupled plasma-enhanced chemical-vapor deposition (ICPECVD), sputter deposition, evaporation, atomic layer deposition (ALD), or combinations thereof. Subsequently, the metal film 44 of anodized alumina is etched away by controlled wet etching, such as buffered oxide etch, or KOH or NaOH, to form the sensor 56.

FIG. 6 illustrates another embodiment of the sensor 56 of FIG. 5. In the illustrated embodiment of FIG. 6, the sensor 58 includes nanostructures 50 having a thin film of the biocompatible material. The sensor 58 may include a non-biocompatible material; the film 60 is made of one or more biocompatible materials listed above. In some embodiments, the film 60 may have a thickness in a range from about 10 nm to about 100 nm.

Figure 7:
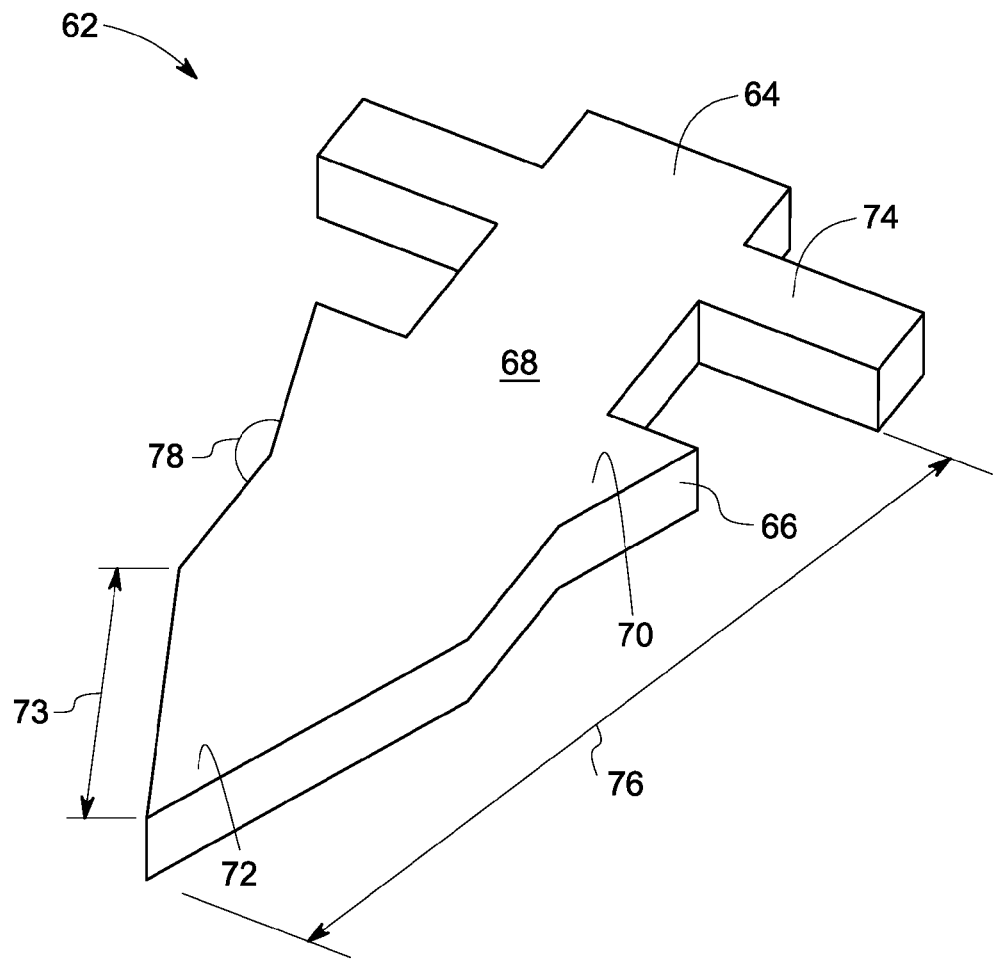
FIG. 7 is a perspective view of a self-adhering solid electrode, in accordance with embodiments of the invention.
Figure 8:
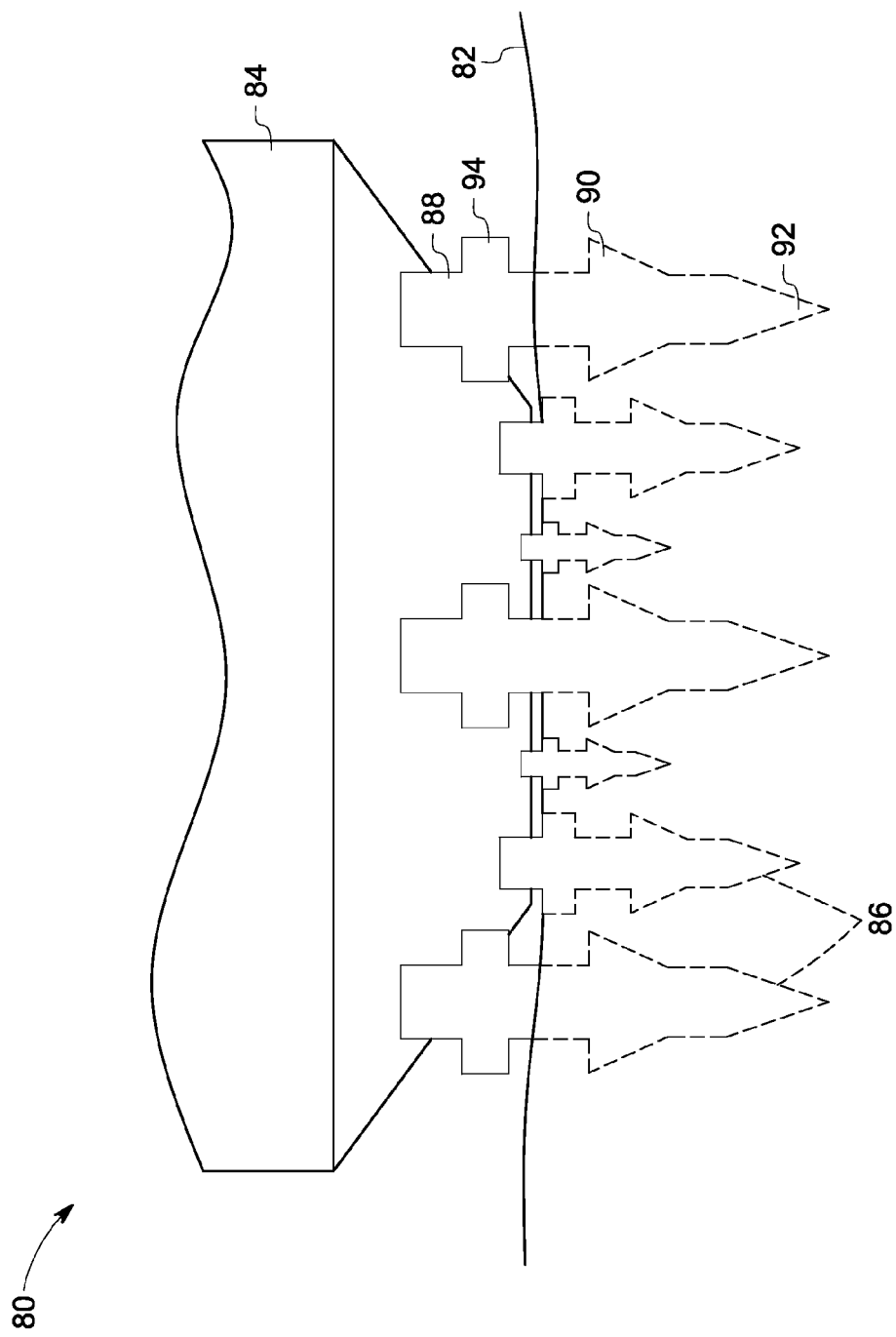
FIG. 8 is a perspective view of a portion of skin employing a self-adhering sensor, in accordance with embodiments of the invention.

Turning now to FIG. 7, a solid electrode 62 is illustrated. The solid electrode 62 is configured to penetrate inside the skin to acquire data for applications such as ECG or EEG monitoring. The dimensions of the electrode 62 may be selected to avoid rupture of the skin and prevent bleeding from the skin. In other words, the penetration of the electrode 62 into the skin should be limited to the stratum corneum, which has a thickness of about 15 micrometers, although, a part of the electrode 62 may be allowed to reach into the upper portion of the epidermis. As illustrated in FIG. 8, an array of the solid electrodes 62 assembled together in a substrate forms a sensor 80. When employed in a sensor array, the solid electrodes, such as electrodes 62, may all have same geometric shapes. Alternatively, some of the solid electrodes may have different geometric shapes. For example, the cross-sections may be selected from a rectangular cross-section, a circular, cross-section, a square cross-section, a triangular cross-section, a hexagonal cross-section, or any other geometrical shape. In the embodiment shown in FIG. 8, the solid electrode 62 comprises a stem 64, which has projections 66. Further, the cross-section of the stem 64 may have different geometric shapes. The stem 64 and the projections 66 are both solid structures. In one embodiment, the solid electrode 62 comprises one or more of silver, gold, platinum, noble metals, or conductive polymers. In another embodiment, the solid electrode 62 may comprise one or more electrically conductive coating. As will be described below, the electrically conductive coating comprises an electrochemical material.

As will be appreciated by one skilled in the art, the figures are for illustrative purposes and are not drawn to scale. Also, although only two projections are illustrated, one on each side of the stem 64, in other embodiments, the projections 66 may be arranged in various configurations, shapes, numbers on the stem 64. The projections may be in a range from about 1 micron to about 100 microns. In some embodiments, the projections 66 are configured to hold the solid electrode 62 inside the skin. The distal end of the stem 64 is pointed to form the tip 72. In some embodiments, the projections 66 may be at an obtuse angle 78 from the surface of the stem 64, which is closer to the distal end of the stem 64 or the tip 72. The distal end or the tip 72 facilitates the insertion of the electrode 62 in the skin. Having the projections 66 at an angle such as angle 78 facilitates insertion of the solid electrode 62 in the skin with a small puncture. Small puncture size reduces the list of infections. The projections 66 may be disposed on the stem in various different configurations, some of the configurations will be described with regard to FIGS. 8-11.

Additionally, the surface 68 may either be smooth or may have textures. In some embodiments, the surface 68 may be a combination of smooth surface and textures. For example, the surface 68 at the tip 72 may be smooth to facilitate penetration of the solid electrode 62 into the skin. The length 73 of the tip 72 may be a few tens of micrometers. However, the texture in the rest of the portion of the stem 64 may be roughened/jagged to facilitate grip of the solid electrode 62 inside the skin. The textures on the surface 68 of the stem 64 may be different at different positions. Further, in some embodiments, the projections 66 may have smooth surface 70. In other embodiments, the surface 70 may be jagged.

Figure 12:
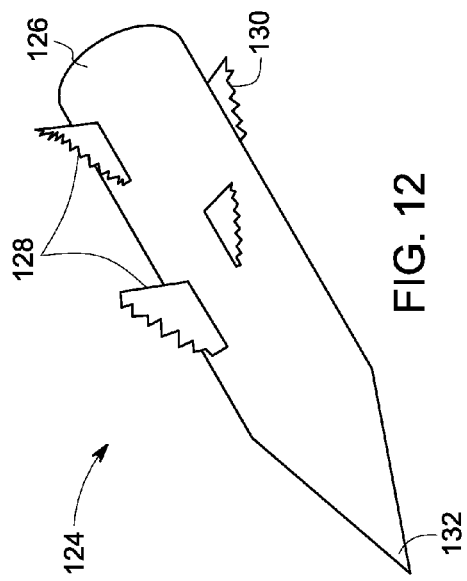
Figure 13:
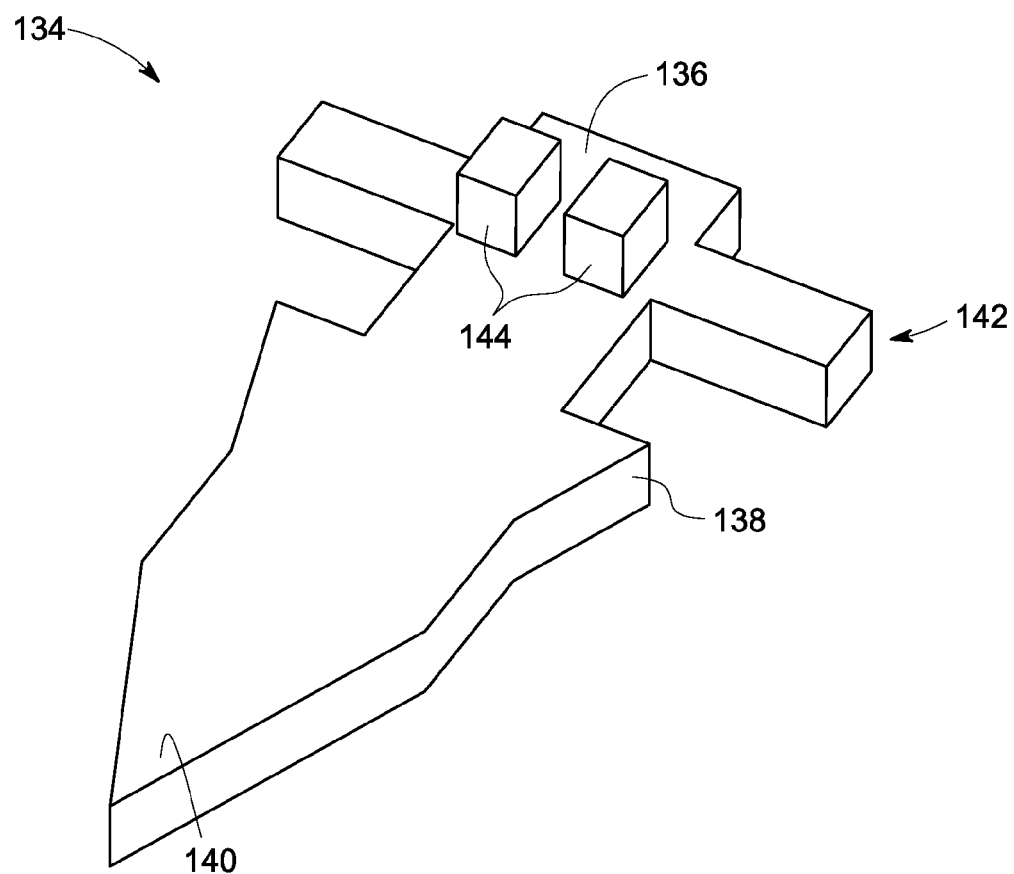
FIGS. 13-17 illustrate embodiments of solid electrodes employing different mechanical stoppers, in accordance with embodiments of the invention.

The solid electrode 62 further includes a mechanical stopper 74 for controlling the extent of the solid electrode 62 penetrating inside the skin. Although not illustrated, the solid electrode, such as the solid electrode 62 may include more than one mechanical stopper 74 so that in instances where the first mechanical stopper coming in contact with the skin fails to stop the penetration of the electrode 62, the next one or two stoppers may be able to prevent further penetration of the electrode in the skin. FIGS. 13-16 illustrate alternate embodiments of the mechanical stopper 74. Once the solid electrode 62 is inserted inside the skin, the mechanical stopper 74 also functions to hold the solid electrode 62 in its position. As illustrated in FIG. 12, the mechanical stopper 74 does not enter inside the skin and remains on the surface. It should be noted that two or more mechanical stoppers 74 may be employed by the solid electrode 62. Additionally, the mechanical stopper 74 may or may not be a continuous structure. As illustrated in the embodiment of FIG. 13, the mechanical stopper 74 may include a plurality of blocks. These pluralities of blocks are positioned such that they act as a mechanical stopper, thereby holding the solid electrode 62.

The mechanical stopper 74 is positioned such that the distance 76 between the tip of the electrode 62 and the mechanical stopper 74 is about a few hundred of micrometers. The dimensions of the electrode 62 may be varied depending on the application. For example, the length of the electrode 62 may be varied depending on the location of the sensor on the body. Also, the dimensions of the electrode 62 may be varied depending on the age of the patient, as the age may be related to the thickness of the skin. For example, when employed in a neo-natal application, the length 76 of the electrode may be reduced to below 50 micrometers to avoid rupturing of the skin.

An electrochemical system may be formed to acquire signals from the electrode 62. The electrochemical system may be formed between the electrode 62, an electrolyte disposed on the electrode 62, and a reference electrode (not shown) disposed outside the sensor. The reference electrode is in electrical communication with the electrode 62. Further, an electrochemical material comprising an electrolyte, such as silver chloride is deposited on the electrode 62. In some embodiments, a separate layer of silver may be deposited before depositing the electrolyte, such as silver chloride, such that a layer of silver exists between the electrode 62 and the layer of silver chloride. In this embodiment, the layer of silver acts as an electrode. Further, the projections 66 of the electrode 62 may have one or more functionality groups coupled to the surfaces 70 of the projections 66.

FIG. 8 illustrates a cross-sectional view of a sensor 80 penetrated inside the skin 82. The sensor 80 includes a biocompatible substrate 84 having a plurality of solid electrodes 86. The sensor 80 requires small pressure to insert the electrodes 86 inside the skin. The pressure required to insert the electrodes 86 inside the skin may be applied by hand. For example, the pressure applied by a thumb of a hand may be sufficient to insert the electrodes 86 inside the skin up to the desired depth. As illustrated, each of the solid electrodes 86 includes a stem 88, projections 90, a tip 92 and a mechanical stopper 94. As noted above, the different solid electrodes 86 may have cross-sections with different geometric shapes. Also, the number of projections 90 employed on an electrode 86 may vary from one stem to another. Additionally, the arrangement of the projections on the stem 88 may be different on different electrodes 86. The mechanical stoppers 94 are configured to hold the solid electrodes 86 in their respective positions, and prevent further penetration of the solid electrodes 86 in the skin 82.

FIGS. 9-12 illustrate alternative embodiments of the solid electrodes 62 and 86. The different type of electrodes may be chosen for the given skin type. Although the embodiments shown in FIGS. 9-12 have stems with circular cross section, it should be noted that the solid electrodes of these embodiments may employ any of the different geometric shapes for the stems. Also, the texture of the stems and the projections in these solid electrodes may be varied depending on the application. Further, different types of mechanical stoppers depicted in FIGS. 13-16 may be employed in the solid electrodes of FIGS. 9-12.

Figure 9:
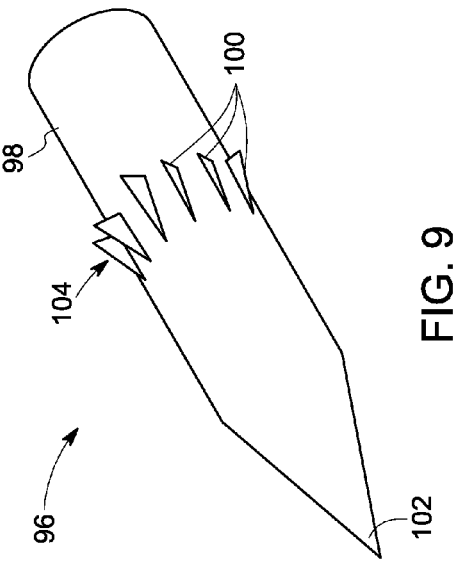
FIGS. 9-12 illustrate embodiments of solid electrodes employing different configurations of projections and surface texture, in accordance with embodiments of the invention.
Figure 10:
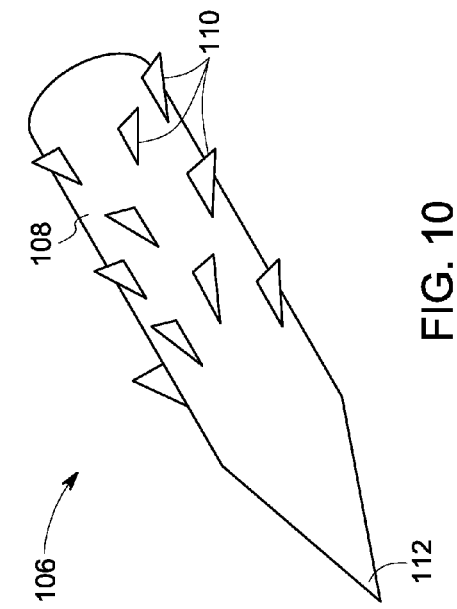

FIG. 9 shows a portion of the solid electrode 96. The solid electrode 96 comprises a stem 98, a plurality of projections 100, and a tip 102. The projections 100 form a projection ring 104. The projection ring 104 employ a plurality of projections 100. The solid electrode 96 may comprise any number of projection rings 104 depending on the application. FIG. 10 illustrates a portion of the solid electrode 106 having a stem 108. The projections 110 are distributed in a random pattern on the stem 108. The stem 108 further includes a tip 112. Although not illustrated, in certain embodiments, the projections 110 may be arranged in one or two rings along the circumference of the stem 108.

Figure 11:
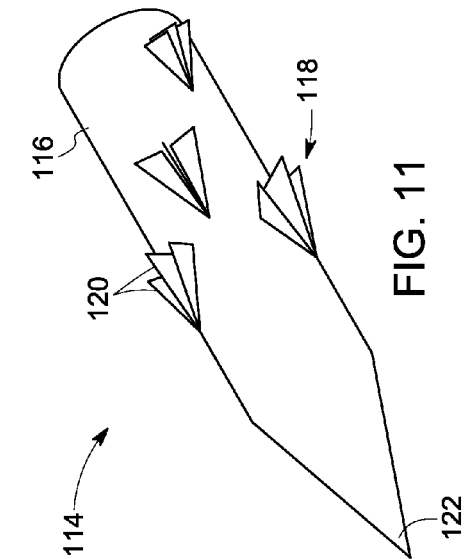

FIG. 11 illustrates a solid electrode 114, having a stem 116. The stem employs clusters 118 of projections 120. Although not illustrated, the different clusters 118 employed on the stem 116 may have varying numbers of projections 120. The solid electrode 114 further comprises a tip 122. FIG. 12 illustrates a solid electrode 124 having a stem 126. The projections 128 employed on the stem 128 have jagged edges 130. The solid electrode 124 further comprises a tip 132.

FIGS. 13-16 illustrate alternative embodiments of a mechanical stopper. Although the embodiments of FIGS. 13-16 illustrate an electrode stem with a rectangular cross-section, it should be noted that any of the other geometrical shapes may be used.

Figure 14:
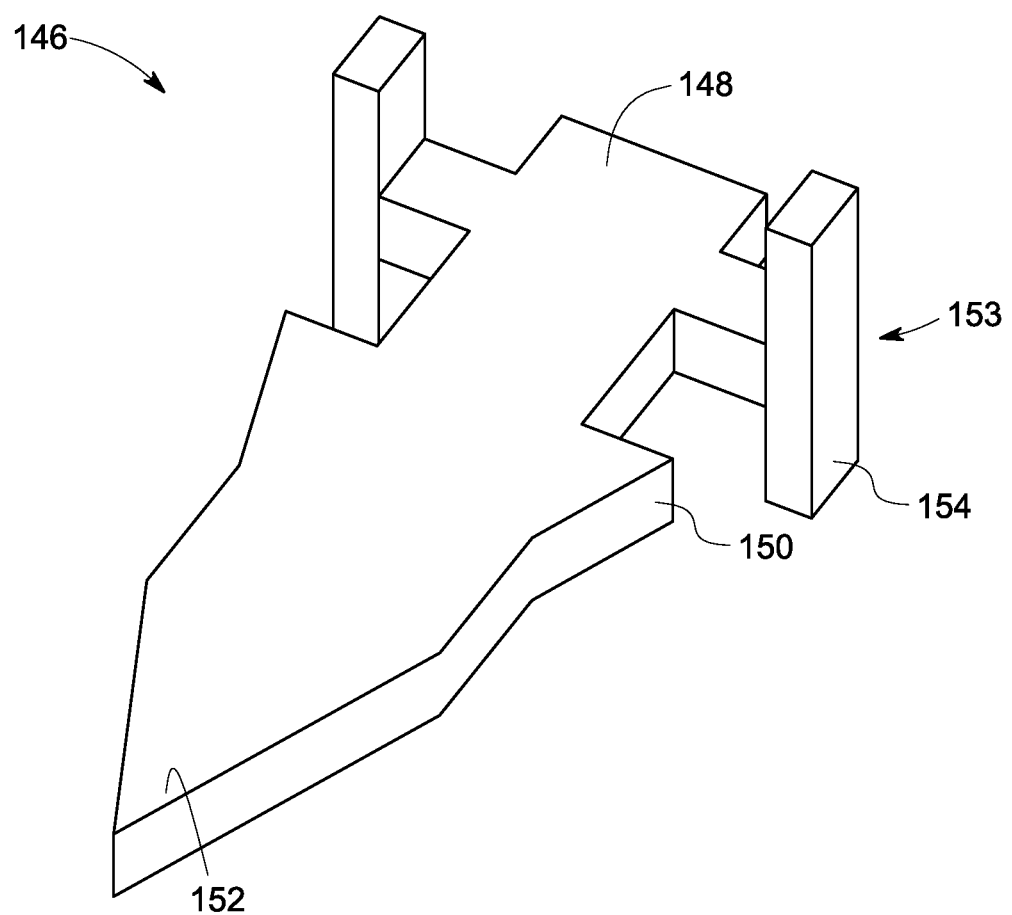
Figure 15:
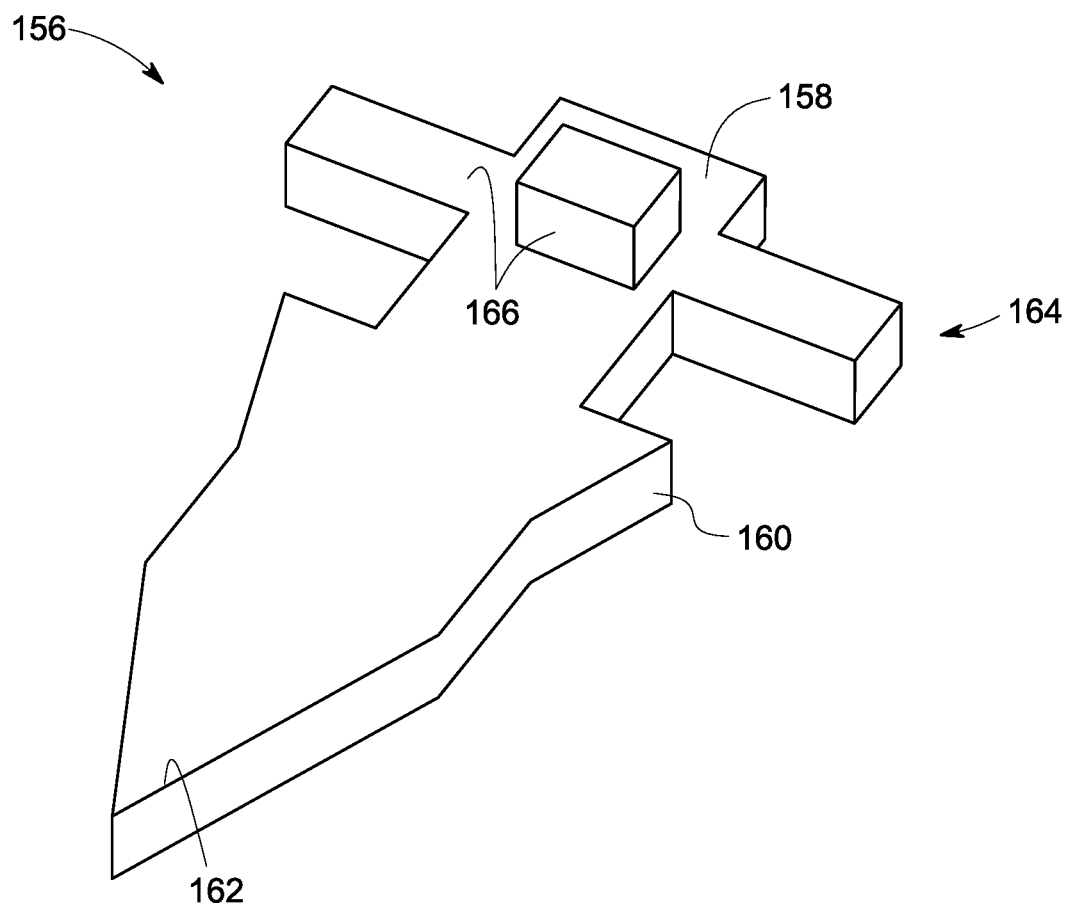
Figure 16:
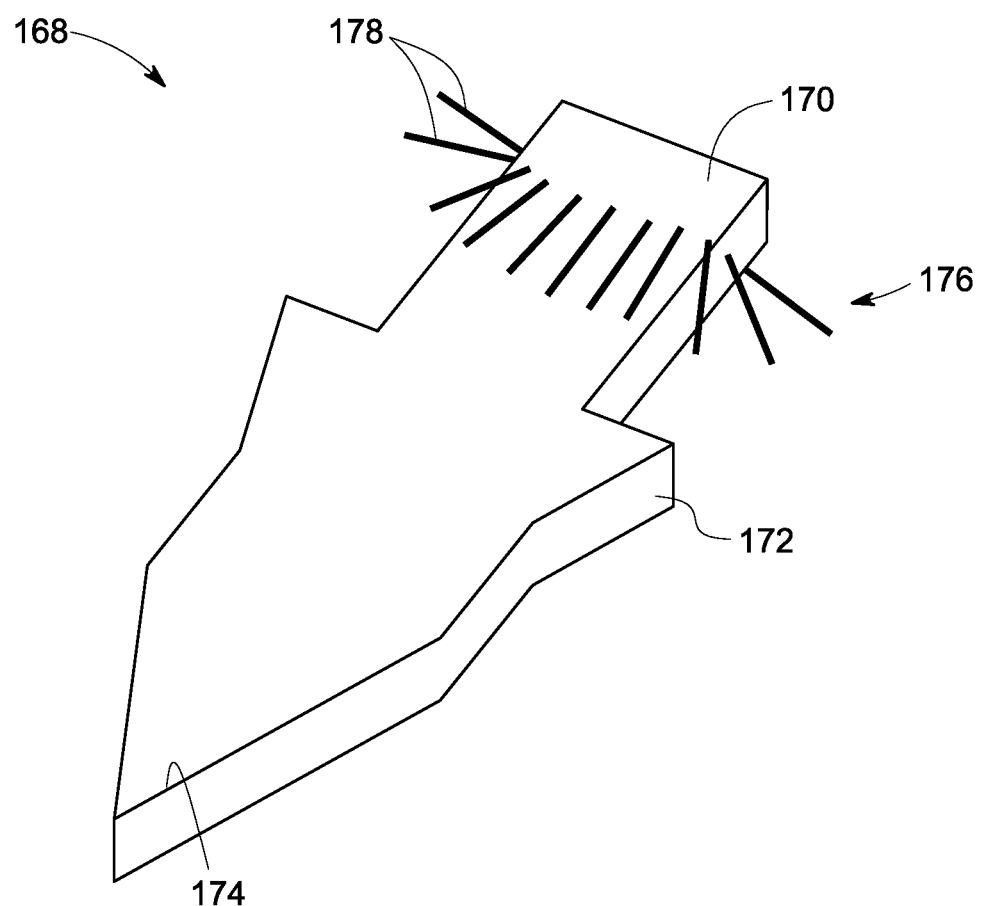

FIG. 13 illustrates a solid electrode 134 having a stem 136, projections 138, a tip 140, and a mechanical stopper 142. The mechanical stopper 142 comprises a plurality of sub-portions 144 which are arranged around the stem 136. FIG. 14 illustrates a solid electrode 146 having a stem 148, projections 150, a tip 152 and a mechanical stopper 153. The mechanical stopper 153 includes two wings 154 disposed on either side of the stem 148. FIG. 15 illustrates a solid electrode 156 having a stem 158, projections 160, and a tip 162. The electrode 156 includes a mechanical stopper 164 having sub-portions 166 disposed on each of the four sides of the stem 158. FIG. 16 illustrates a solid electrode 168 having a stem 170, projections 172 and a tip 174. The electrode 168 further includes a mechanical stopper 176. The stopper 176 includes a plurality of spikes 178 arranged around the stem 170.

Figure 17:
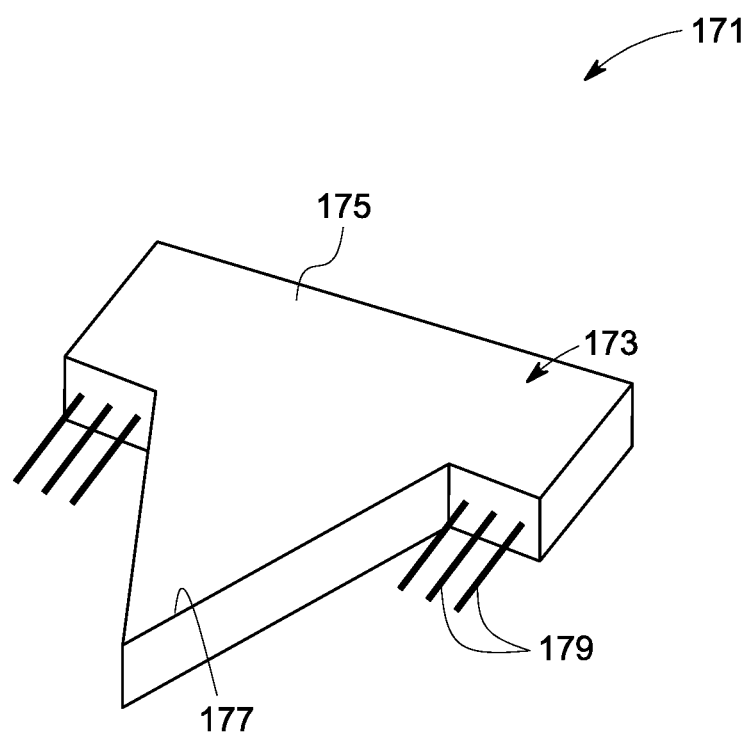

FIG. 17 illustrates a composite electrode 171 having a solid electrode 173. The solid electrode 173 includes a stem 175, the stem also acts as a mechanical stopper for the electrode 171. The solid electrode 173 further includes a tip 177. The electrode 171 further includes a plurality of nanostructures 179. The nanostructures 179 are configured to promote adhesion of the electrode 171 to the skin. Additionally, the nanostructures 179 are configured to acts as electrodes and take measurements from the patient's body. Accordingly, in the composite electrode 171, the measurements may be taken from both the tip 177 and the nanostructures 179.

As with the composite electrode 171 of FIG. 17, the nanostructure, such as nanostructure 179, may be used with any of the above mentioned solid electrodes of FIGS. 7-16. The composite electrode may be formed by coupling the nanostructures on a plastic substrate formed by the method of FIGS. 3-6 to any of the solid electrodes of FIGS. 7-16

Figure 18:
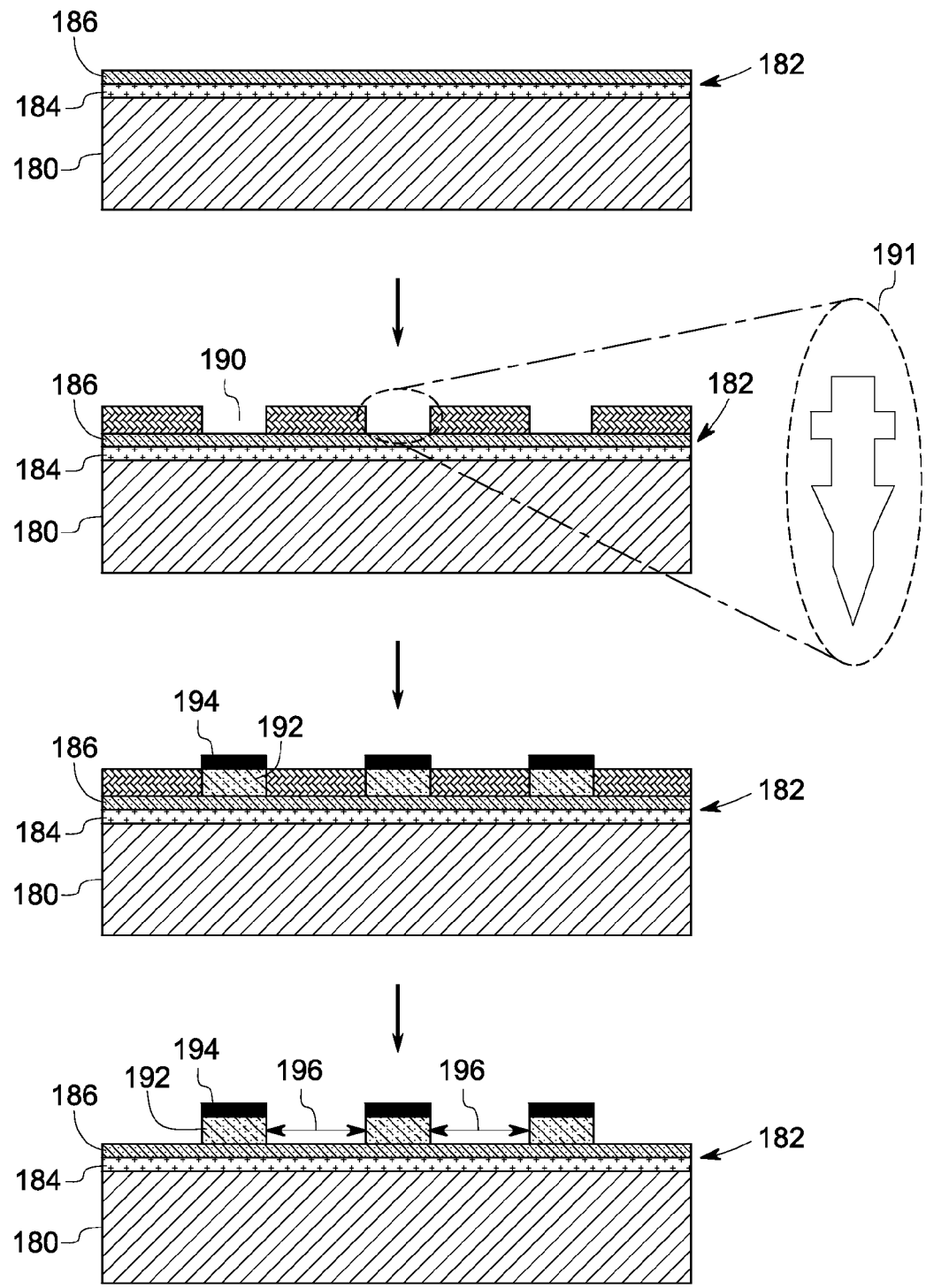
FIG. 18 is a schematic illustration of an exemplary method of making a solid electrode, in accordance with embodiments of the invention.

FIG. 18 illustrates an example of the method for forming solid electrodes, such as the solid electrodes illustrated in FIGS. 7-16. The method comprises the step of providing a substrate 180 having a seed layer 182. In the illustrated method, the seed layer 182 comprises two layers 184 and 186. The bottom seed layer 184 is an adhesion promoter layer to provide better adhesion between the seed layer 182 and the substrate 180. For example, the bottom layer 184 may include titanium, chromium, or nickel. The top seed layer 186 comprises a conductive material, such as copper, to facilitate deposition process such as electroplating. Although not illustrated, in some embodiments, the seed layer 182 may comprise more than two layers. Further, a photo resist layer 188 is deposited and patterned to form patterns 190 in the photo resist layer 188.

The top view of the pattern 190 is depicted in the dotted circle 191. As illustrated the pattern 190 imitates the structure of the desired solid electrode. Further, the material of the solid electrode is then deposited in the pattern 190 by methods such as electroplating to form the electrode 194, such as physical vapor deposition, plasma-enhanced chemical-vapor deposition (PECVD), radio-frequency plasma-enhanced chemical-vapor deposition (RFPECVD), expanding thermal-plasma chemical-vapor deposition (ETPCVD), reactive sputtering, electron-cyclodrawn-residence plasma-enhanced chemical-vapor deposition (ECRPECVD), inductively coupled plasma-enhanced chemical-vapor deposition (ICPECVD), sputter deposition, evaporation, atomic layer deposition (ALD), or combinations thereof. Further, a conductive material layer 194 is deposited on the electrode material 194. The conductive material layer 194 may comprise silver. Subsequently, the photo resist 188 is dissolved from in between the electrodes to form a pattern 196 in the photo resist 188 to form a sensor array having the substrate 180 and a plurality of electrodes 192 with conductive material coating 194. The method illustrated in FIG. 18, facilitates bulk production of the electrodes, such as the electrode 192.

Figure 19:
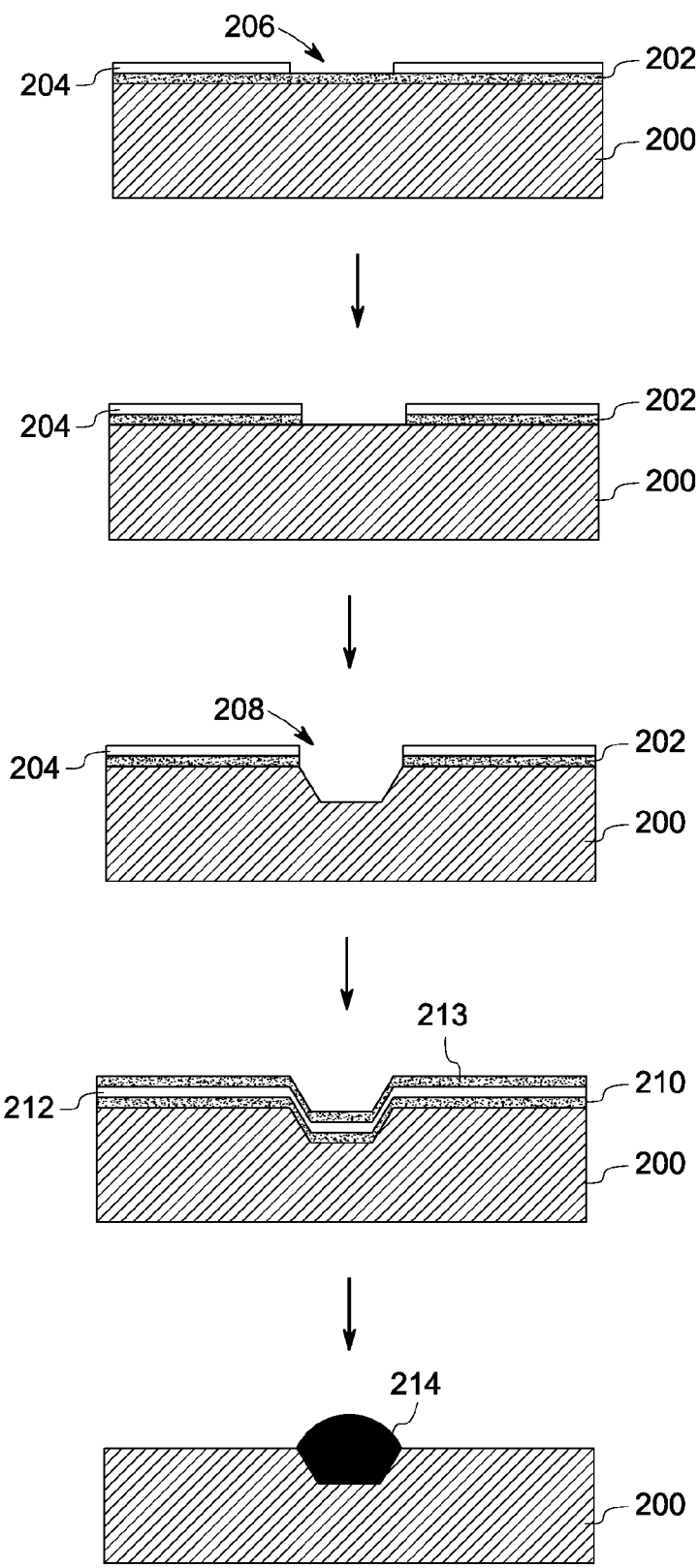
FIG. 19 is a schematic illustration of an exemplary method of making solid electrodes having different cross sections, in accordance with one or more embodiments.

FIG. 19 illustrates a method of making solid electrodes with varying geometric shapes. While employing geometric shapes with sharper edges the force required to insert the electrode in the skin is reduced due to the sharper tips. The method includes providing a substrate 200. The substrate 200 may be made of a semiconductor, a ceramic, and a polymer. In one example, the substrate 200 may be made of silicon. In another example, the substrate 200 may be a printed circuit board. Further, an etching layer 202 is deposited on the substrate 200. The etching layer may include an oxide or a nitride. Suitable examples of etching layer materials may include silicon nitride, or silicon oxide. Further, a photo resist layer 204 is deposited on the etching layer 202. The photo resist layer facilitates selective removal of a portion of the etching layer 202 to form an opening 206 in the etching layer 202. Subsequently, the substrate 200 is etched to create a predetermined pattern. In the illustrated embodiment, a hexagonal shape 208 is formed by controlled etching. Suitable etching may include wet etching, or chemical etching. The etching may be isotropic or anisotropic etching depending on the predetermined shape of the etched pattern. Next, the etching layer 202 and the photo resist layer 204 are removed. Subsequently, a first seed layer 210 comprising for example, titanium, is deposited on the etched pattern. The first seed layer 210 promotes adhesion and also promotes removal of the seed layers from the substrate during later stages of the processing. The second seed layer 212 is deposited on the first layer. The second seed layer 212 facilitates electroplating. The second seed layer 212 comprises a conductive metal, such as copper. After depositing the two seed layers 210 and 212, one more coating of the material of the first seed layer 210 is deposited to form a layer 213. Subsequently, the metal layer 214 may be deposited in the pattern 208 by electroplating and the seed layers 210 and 212 may be removed thereafter. As illustrated, the layer 214 acquires a shape similar to the shape 208, thereby producing solid electrodes with different cross-sections.

Figure 20:
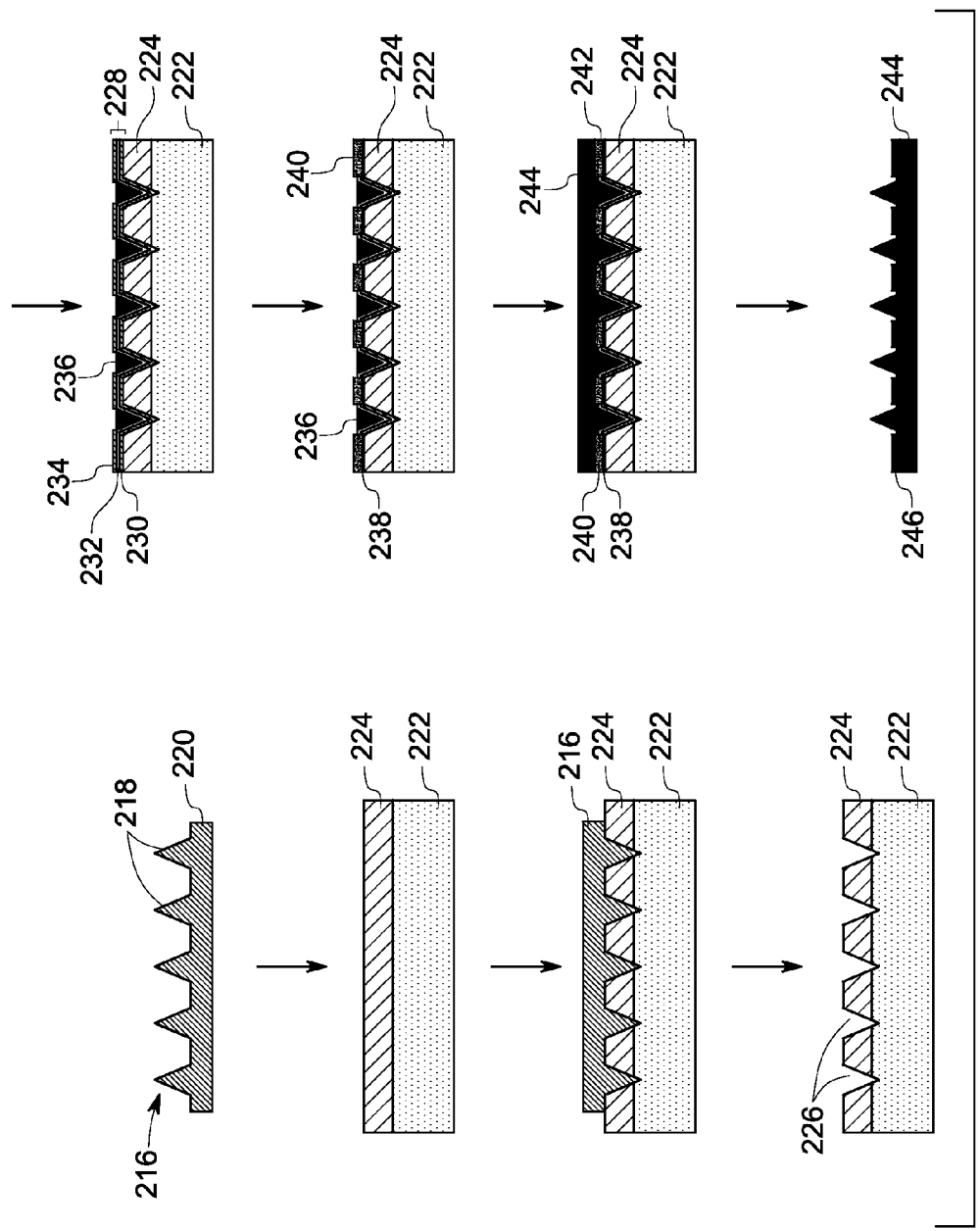
FIG. 20 is a schematic illustration of various steps involved in an exemplary method of the invention for making a self-adhering non-invasively coupled composite electrode, in accordance with one or more embodiments.

FIG. 20 illustrates a method of forming a composite electrode, such as the electrode illustrated in FIG. 17, having both a solid electrode and nanostructures. The method of this example begins by providing a structure 216. The structure 216 is for illustrative purposes and various alternatives of the structure 216 may be used in the referenced method. In the illustrated embodiment, the structure 216 comprises a plurality of tapered needles 218 coupled together by a common base 220. In some embodiments, such a structure 216 may be formed by laser drilling. The needles 218 may comprise silicon or any other suitable material. Also provided is a substrate 222 with a sacrificial layer 224. The substrate 222 may be made of ceramic, polymer, glass, or semiconductor material. The sacrificial layer 224 is configured to deform permanently upon application of pressure. The sacrificial layer 224 may include a polymer. The sacrificial layer 224 may either be directly deposited on the substrate 222 or may be formed separately and then coupled to the substrate 222. The structure 216 is then disposed on the substrate 222 having the sacrificial layer 224 such that the needles 218 penetrate into the sacrificial layer 224 when the pressure is applied on the structure 216. Subsequently, the structure 216 is removed from the substrate 222 and a sacrificial layer 224 is obtained which replicates the pattern of the structure 216 and forms cavities 226 in the sacrificial layer 224. Subsequently, a seed layer 228 having three layers 230, 232 and 234 is deposited on the sacrificial layer 224. In one example, the layers 230, 232 and 234 are made of titanium, copper and titanium, respectively. The cavities 226 are then filled with a material 236 suitable for use in solid electrodes as noted above. The cavities 226 may be filled by employing electroplating.

Subsequently, the seed layer 228 is removed from the portions of the polymer layer that are outside the cavities 226. An adhesion-promoting layer 238 is deposited on the exposed portions of the sacrificial layer 224, as illustrated. The adhesion-promoting layer 238 may include titanium. Further, an aluminum layer 240 is deposited on the adhesion-promoting layer 238. The aluminum layer 240 is configured to form pores upon anodization. The layer 240 may also employ any other metal other than aluminum which is capable of forming pores upon anodization. The aluminum layer 240 is anodized and the pores 242 so formed are filled with a conductive material, such as silver, platinum, gold, noble metals, or any other metal which may be suitable for use in nanostructures. The pores 242 may be filled by dipping the aluminum layer 240 in a bath of the conductive material. Subsequently, the base layer 244 is deposited by electroplating. The substrate 222 and the sacrificial layer 224 are then decoupled from the rest of the structure. The decoupling may be done by dissolving the sacrificial layer. The sacrificial layer may be dissolved by wet etching. Subsequently, anodized aluminum layer 240 is dissolved by etchants as noted above with regard to FIGS. 3-6. The dissolution of the anodized layer 240 yields nanostructures 246 that are coupled to the base layer 244.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A self-adhering sensor for non-invasively attaching to a portion of a skin, comprising:
   a biocompatible substrate made of a ceramic, a polymeric material, or both; and
   an array of solid nanoelectrodes coupled to the biocompatible substrate and configured to self-adhere to the skin, wherein the solid nanoelectrodes comprise one or more conductive materials selected from a group consisting of: silver, gold, platinum, noble metals, and conductive polymers, wherein a length of the nanoelectrodes in the array of solid nanoelectrodes is less than or equal to about 1 micrometer, and
   wherein the self-adhering sensor is configured to couple to the portion of the skin using Van der Waals forces.

2. The sensor of claim 1, wherein one or more of the solid nanoelectrodes comprise a cross-section that is substantially rectangular, circular, square, triangular or hexagonal.

3. The sensor of claim 1, wherein one or more of the solid nanoelectrodes comprise one or more functionality groups coupled to a surface of the solid nanoelectrodes.

4. The sensor of claim 1, wherein a diameter of the solid nanoelectrodes is in a range from about 10 nanometers to about 500 nanometers.

5. The sensor of claim 1, wherein the sensor is an electroencephalography sensor.

6. The sensor of claim 1, wherein the sensor is an electrocardiography sensor.

7. The sensor of claim 1, wherein the sensor is a neonatal sensor.

8. A method of non-invasively coupling a sensor to a portion of a skin, comprising:
   providing a sensor, comprising:
      a biocompatible substrate made of a ceramic, a polymeric material, or both; and
      an array of solid nanoelectrodes configured to self-adhere to the skin, wherein the solid nanoelectrodes are coupled to the biocompatible substrate, wherein the solid nanoelectrodes comprise one or more conductive materials selected from a group consisting of silver, gold, platinum, noble metals, and conductive polymers, and wherein a length of the nanoelectrodes in the array of solid nanoelectrodes is less than or equal to about 1 micrometer; and
   coupling the sensor by pressing the sensor against a surface of the skin so that at least a portion of one or more of the solid nanoelectrodes engages the surface of the skin using Van der Waals forces.

9. The method of claim 8, wherein the sensor does not penetrate the skin.

* * * * *